United States Patent

Takanohashi et al.

[11] Patent Number: 5,902,885
[45] Date of Patent: May 11, 1999

[54] PRODUCTION OF L-ASCORBIC ACID

[75] Inventors: Kunio Takanohashi, Kawanishi; Mitsutaka Tanaka, Sanda; Toru Yamano, Itami, all of Japan

[73] Assignee: Takeda Chemical Industries, Ltd., Japan

[21] Appl. No.: 08/002,513

[22] Filed: Jan. 8, 1993

Related U.S. Application Data

[63] Continuation of application No. 07/866,092, Apr. 6, 1992, abandoned, which is a continuation of application No. 07/723,653, Jun. 26, 1991, abandoned, which is a continuation of application No. 07/204,527, Jun. 8, 1988, abandoned.

[30] Foreign Application Priority Data

Jun. 8, 1987 [JP] Japan .................................. 62-142504

[51] Int. Cl.$^6$ .................................................. C07D 307/62
[52] U.S. Cl. ............................................................ 549/315
[58] Field of Search .............................................. 549/315

[56] References Cited

U.S. PATENT DOCUMENTS

| 2,185,383 | 1/1940 | Pasternack et al. | 260/344 |
| 2,462,251 | 2/1949 | Bassford et al. | 549/315 |
| 4,491,668 | 1/1985 | Ikawa et al. | 549/315 |

FOREIGN PATENT DOCUMENTS

| 43-9217 | 4/1968 | Japan . |
| 48-15931 | 5/1973 | Japan . |
| WO/8700839 | 2/1987 | WIPO . |

*Primary Examiner*—Ba K. Trinh
*Attorney, Agent, or Firm*—Wenderoth, Lind & Ponack, L.L.P.

[57] ABSTRACT

L-ascorbic acid is produced by allowing an acid to act on 2-keto-L-gulonic acid in a mixture solvent of an inert organic solvent and an aliphatic ketone in the presence of water and a surfactant.

The method produces L-ascorbic acid in a high yield 90% or more and is an industrially advantageous method.

5 Claims, No Drawings

PRODUCTION OF L-ASCORBIC ACID

This application is a continuation of now abandoned application, Ser. No. 07/866,092, filed on Apr. 6, 1992, which is a continuation of now abandoned application Ser. No. 07/723,653, filed Jun. 26, 1991, which is a continuation of now abandoned application Ser. No. 07/204,527, filed Jun. 8, 1988 all now abandoned.

This invention relates to a method of preparing L-ascorbic acid, in which 2-keto-L-gulonic acid is employed as the starting material.

As one of the methods of preparing L-ascorbic acid, there has been known a method which comprises employing 2-keto-L-gulonic acid as the starting material and allowing an acid to act thereon to prepare L-ascorbic acid in one step.

The known methods include, for example, ① a method which comprises allowing concentrated hydrochloric acid to act on 2-keto-L-gulonic acid using acetic acid as the solvent [U.S. Pat. No. 2,185,383 Specification (1940)], ② a method which comprises adding ethanol and acetone to sodium salt of 2-keto-L-gulonic acid, neutralizing with hydrochloric acid, separating precipitating sodium chloride by filtration, then maintaining the reaction mixture at temperatures ranging from 25° C. to 75° C. to thereby obtain L-ascorbic acid Japanese Unexamined Pat. Pub. No. 58-177986, ③ a method which comprises allowing a mineral acid to act on 2-keto-L-gulonic acid in an inert solvent in the presence of a surfactant (Japanese Examined Pat. Pub. No. 48-15931) and ④ a method which comprises causing slurry of substantially anhydrous 2-keto-L-gulonic acid to be produced in an inert organic solvent containing a surfactant, then allowing a substantially anhydrous acid catalyst to act on this slurry to give L-ascorbic acid [PCT,WO87/00839 (1987)].

On the other hand, fermentative methods of preparing 2-keto-L-gulonic acid in a large amount from L-sorbose have been proposed (e.g. U.S. Pat. No. 4,543,331, EP 132,308), and thus a method of industrial production of L-ascorbic acid at one stroke by using this starting material has been desired to be established as early as possible.

However, the known methods mentioned above have still some drawbacks, while, some improvement is observed in e.g. yield, including still insufficient yield from the viewpoint of industrial production, a large content of colored substances in the reaction mixture as impurities, which inevitably imposes a burden on the purification process, thus preventing them from being employed as methods in an industrial scale.

The present inventors have conducted study on methods of preparing L-ascorbic acid employing 2-keto-L-gulonic acid as the starting material, and have established an industrially advantageous method affording a high yield of about 90% or more of the desired product with little production of impurities More specifically, the present inventors have found that the reaction proceeds advantageously by conducting lactonization of 2-keto-L-gulonic acid in a mixture solvent of an inert organic solvent e.g. toluene, benzene, etc. and an aliphatic ketone e.g. acetone, methyl ethyl ketone, etc. And, the present inventors have also found that the reaction proceeds more advantageously by suitably controlling the amounts of water and an acid catalyst.

Namely, the present invention relates to a method of preparing L-ascorbic acid, which comprises allowing an acid to act on 2-keto-L-gulonic acid in a mixture solvent of an inert organic solvent and an aliphatic ketone in the presence of water and a surfactant.

The reaction of this invention is conducted in a mixture solvent prepared by adding a given amount of an aliphatic ketone to an inert organic solvent.

The inert organic solvent means an organic solvent with which 2-keto-L-gulonic acid and L-ascorbic acid are not reactive and in which 2-keto-L-gulonic acid and L-ascorbic acid are insoluble.

Inert organic solvents usable for the present invention include aromatic hydrocarbons which may be substituted with halogen or alkyl, such as benzene, toluene, xylene and chlorobenzene; halogenated aliphatic hydrocarbons such as chloroform and ethylene chloride; aliphatic hydrocarbons such as hexane, heptane and octane; and ethers such as tetrahydrofuran, dioxane and isopropyl ether; or a mixture of them. Preferable ones are aromatic hydrocarbons such as benzene or toluene.

Aliphatic ketones usable for the present invention include ketones containing alkyl having 1 to 6 carbon atoms, and cyclic ketones containing cycloalkyl having 5 to 6 carbon atoms.

The alkyl may be straight-chain or branched one, preferably a one having 1 to 4 carbon atoms. These two alkyls bonding to carbonyl may be the same as or different from each other. Practical examples of such ketones include acetone, methyl ethyl ketone, diethyl ketone, methyl isobutyl ketone and cyclohexanone, preferably acetone and methyl ethyl ketone.

Such a ketone as exemplified above is required to be present in a specified amount in an inert organic solvent. The amount of a ketone to be mixed is about 0.02 to 0.3 volume part, preferably 0.05 to 0.2 volume part, relative to 1 volume part of an inert organic solvent. By maintaining the ketone concentration within this range throughout the reaction, the reaction can be allowed to proceed more smoothly. And, the ketone may be supplemented in the course of the reaction, so long as the amount of ketone does not deviate the above-mentioned range.

When the amount of a ketone to be mixed is out of the range specified as above, the amount of degradation products increases to cause more strong coloration of the reaction mixutre, thus complicating the purification procedure, which is far from an industrially advantageous method. When the amount of a ketone exceeds the above-mentioned range, the amount of unreacted materials tends to become more, thus lowering the yield of the object compound.

In this invention, the lactonization of 2-keto-L-gulonic acid is carried out in the above-mentioned mixutre solvent. The concentration of 2-keto-L-gulonic acid relative to the mixtrue solvent is not limitative, but is usually 5 to 40 weight %, preferably 10 to 30 weight % from the economical viewpoint.

In the present invention, the reaction is allowed to proceed by adding an acid in the presence of water and a surfactant. In this case, the amounts of water and an acid are preferably restricted as follows, respectively. The amount of water is 1.5 to 3.5 times as much in molar ratio, preferably 1.8 to 3 times as much in molar ratio relative to 2-keto-L-gulonic acid. Water is allowed to be present within the mentioned range in the solvent when the reaction is carried out. When the starting material 2-keto-L-gulonic acid is, for example, hydrated or contains water, such water is taken into account for calculation of the amount of water. And, the amount of water contained in an acid catalyst used for promoting the reaction or in a mixture solvent then employed is also taken into account for calculation of the amount of water. When the amount of water deviates from the above-mentioned range, the amount of decomposed materials increases to cause lowering of the yield.

Surfactants that can be used in this invention include nonionic surfactants such as polyoxyethylene alkylaryl ether, polyoxyethylene alkyl ether, etc, cationic surfactants such as quarternary ammonium salts, pyridinium salts, etc., and anionic surfactants such as higher aliphatic alkylaryl sulfonates, etc.; each surfactant may be used alone or in combination with one or more of them Desirable surfactants for this invention are cationic ones, especially quaternary ammonium salts such as trimethyl tetradecyl ammonium chloride, trimethyl dodecyl ammonium chloride, trimethylcetyl ammonium chloride, trimethyloctyl ammonium chloride, diiethylethylcetyl ammonium chloride, trimethylstearyl ammonium chloride, dimethyl butylcetyl ammonium bromide and trimethyldodecyl ammonium bromide. The amount of the surfactant to be added ranges from 0.01 to 10 w/w %, preferably from 0.05 to 3.0 w/w % relative to 2-keto-L-gulonic acid.

Acids employable as the catalyst are exemplified by mineral acids including, for example, hydrochloric acid, phosphoric acid, etc., and hdyrochloric acid is espacially preferable The amount of an acid to be added for allowing the reaction to proceed advantageously, in the presence of water of an amount within the above-mentioned range, is 0.5 to 2 times as much in molar ratio, preferably 0.5 to 1.5 times as much in molar ratio relative to 2-keto-L-gulonic acid. As water is required for the reaction, it is preferable to employ hydrochloric acid of 20 to 45% concentration, usually a one having 35% concentration. The ketone solution containing hydrogen chloride is employable for adjusting the amount of an acid. Addition of an acid may be conducted in two installments within the above-mentioned range.

Under the above-mentioned conditions, the starting material 2-keto-L-gulonic acid is lactonized by the action of an acid to give L-ascorbic acid. The reaction proceeds in a heterogenous system. As the reaction proceeds, 2-keto-L-gulonic acid becomes gruel-like to oily (usually in 30 minutes to one hour after initiating the reaction). At this point of time, it is preferable to adjust the amounts of water and acid to the given ones. It is also possible to adjust the volume of water remaining in the reaction mixture by eliminating water in the reaction mixture by means of a conventional dehydrating procedure such as azeotropic distillation. This dehydration process is preferable to complete within a period as short as possible. When an aliphatic ketone or an acid catalyst is distilled off together with water, for example, by azeotropic dehydration, they may be suitably supplemented. Reaction temperatures range from about 40° C. to about 80° C., preferably from 50° C. to 70° C. The recation completes usually in 3 to 8 hours.

For separating the object compound from the reaction mixture, a per se conventional process, for example, filtration, concentration, extraction, etc is employable. Further, if necessary, the object compound may be led to a highly purified one through, for example, recrystallization.

According to the method of this invention, L-ascorbic acid can be prepared in a high yield of 90% or more. In addition, due to a little amount of impurities (e.g decomposition products) which may cause coloring occurs, no troublesome purification process is required, which is of a very industrial advantage. The following Examples and Comparative Examples will explain the present invention in more detail.

EXAMPLE 1

To a mixture solvent of toluene (570 ml) and acetone solution containing 23.5 weight % of hydrogen chloride (65 ml as acetone) was added 2-keto-L-gulonic acid (content 91.2%, water content 8.4%)(100 g). To this solution were further added water (7.7 ml) and trimethylcetylammonium chloride (110 mg)(water content was 1.90 times as much in molar ratio relative to 2-keto-L-gulonic acid). The reaction mixture was stirred for six hours while heating at 60° C., which was then cooled to 20° C. The resultant was poured into water (1 l), and the mixture was stirred, which was then left standing, followed by separating the aqueous layer. To the organic layer was added water (400 ml) for re-extraction. The aqueous layers were combined and subjected to quantitative determination by means of a high performance liquid chromatography to reveal the existence of L-ascorbic acid [78.2 g (yield 94.5%)], while unreacted 2-keto-L-gulonic acid remaining in an amount of 2.7%. The absorbance ($E_{430_{nm}}^{1\%}$) of this aqueous layer was 0.160.

The high performance liquid chromatography was conducted under the following conditions (the same applies to all the subsequent Examples and Comparative Examples).

Column: Aminex HPX-87H manufactured by Bio Rad Co.

Eluent: 0.1M ammonium sulfate

Column temperature: room temperature

Detection e $UV_{210}$ nm and refractive index

EXAMPLE 2

To a mixture solvent of toluene (576 ml) and acetone (30 ml) was added 2-keto-L-gulonic acid (content 89.9%, water content 8.4%) (101.4 g), to which was added trimethyltetradecylammonium chloride (110 mg), followed by further addition of 35% hydrochloric acid (10 ml)(d=1.17, 4.1 g as HCl, 7.7 g as water). The water content in the reaction mixture was calculated to be 16.2 g (1.19 times as much in molar ratio relative to 2-keto-L-gulonic acid).

The reaction mixture was heated at 60° C. and stirred for one hour to cause the crystals of 2-keto-L-glulonic acid to become oily, to which was added an acetone solution containing hydrogen chloride (15.8 weight %) (51. 8 g) (8.18 g as HCl, 55 ml as acetone). The whole mixture was stirred for 5 hours at the same temperature, which was then cooled to 20° C.(the total amount of acid relative to 2-keto-L-gulonic acid was 0.72 times as much in molar ratio).

The reaction mixture was poured into water (1 l), which was stirred, then was left standing. The aqueous layer was separated. To the organic layer was further added water (600 ml) for re-extraction. The aqueous layers were combined.

Quantitative determinaiton of the resultant L-ascorbic acid by means of a high performance liquid chromatography revealed that 77.7 g (yield: 94.0%) of the compound was produced, while 2-keto-L-gulonic acid remained unreacted in an amount of 2.3% ,The absorbance ($E_{430_{nm}}^{1\%}$) of this reaction mixture was 0.17.

EXAMPLE 3

To a mixture solvent of toluene (576 ml) and methyl ethyl ketone (24 ml) was added 2-keto-L-gulonic acid (content 89,9%, water content 8.4%) (101.4 g), to which was added trimethylcetyl ammonium chloride (110 mg), followed by further addition of 35% hydrochloric acid (13.2 ml) (d=1.17, 5.4 g as HCl, 10.0 g as water). The water content in the reaction mixture was calculated to be 18.5 g (2.14 times as much in molar ratio relative to 2-keto-L-gulonic acid).

The reaction mixture was stirred for one hour at 60° C., then crystals of the 2-keto-L-gulonic acid became oily, to which was added a methyl ethyl ketone solution containing 18 weight % hydrogen chloride (45 g) (8.1 g as HCl, 46 ml as methyl ethyl ketone). The whole mixture was stirred for 5 hours at the same temperature, followed by cooling to 20°

C. (the total amount of acid relative to 2-keto-L-gulonic acid was 0.79 times as muchlin molar ratio).

The reaction mixture was poured in water (1 l), which was stirred, then left standing, followed by separating the aqueous layer. To the organic layer was added water (600 ml) for re-extraction, and the aqueous layers were combined.

Quantitative determination of the resultant L-ascorbic acid by means of a high. performance liquid chromatography revealed that the 76.9 g (yield: 93.0%) of the compound was produced, while 2-keto-L-gulonic acid remained unreacted in an amount of 2.0%. The absorbance ($E_{430nm}^{1\%}$) of the reaction mixture was 0.155.

EXAMPLE 4~6

Completely the same procedure as that in Example 2 was conducted, excepting using, in place of methyl ethyl ketone, methyl isobutyl ketone, diethyl ketone or cyclohexanone, respectively, to obtain the following results.

| Example No. | Yield of L-ascorbic acid (%) | Color Absorbance ($E_{430\ nm}^{1\%}$) |
|---|---|---|
| 4(isobutyl ketone) | 91.6 | 0.160 |
| 5(diethyl ketone) | 92.7 | 0.162 |
| 6(cyclohexanone) | 92.4 | 0.170 |

EXAMPLE 7

To a mixture solvent of benzene (180 ml) and acetone (20 ml) was added 2-keto-L-gulonic acid (content 91.2%, water content 8.4%)(32 g), to which was added trimethyloetylammonium chloride (140 mg), followed by further addition of 35% hydrochloric acid (10 ml)(d=1.17, 4.09 g as HCl). The water content in the reaction mixture was calculated to be 10.3 ml (3.8 times as much in molar ratio relative to 2-keto-gulonic acid). The reaction mixture was stirred for one hour at 60° C., then crystals of 2-keto-L-gulonic acid became oily, followed by subjecting the reaction mixture to distillation by means of a Soxhlet extractor to distill off about 8 ml as distillate (aqueous layer) under reduced pressure. It was revealed that the aqueous layer was composed of water (3.8 g), acetone (3.0 g) and HCl (0.8 g).

The solution was stirred for 5 hours at the same temperature, which was then cooled to 20° C. The reaction mixture was poured into water (300 ml), stirred and left standing, followed by separating the aqueous layer. To the organic layer was added water (200 ml) for re-extraction. The aqueous layers were combined and subjected to a high performance liquid chromatography to quantitatively determine the L-ascorbic acid produced to reveal that the compound was produced in an amount of 24.9 g (yield: 94.1%) and the 2-keto-L-gulonic acid remained unreacted in an amount of 4.6%. The absorbance ($E_{430nm}^{1\%}$) of the aqueous layer was 0.170.

EXAMPLE 8

To a mixture solvent of benzene (90 ml) and acetone (8 ml) was added 2-keto-L-gulonic acid (15 g)(content: 99.4%, water content: 0.5%), to which were added trimethylcetylammonium chloride (100 mg) and 35% hydrochloric acid (6 m,)(d=1.17, 2.46 g as HCl). The water content in the reaction mixture was calculated to be 4.6 g (3.3 times as much in molar ratio relative to 2-keto-gulonic acid). The reaction mixture was stirred for about 75 minutes at 60 to 65° C. to give an oily 2-keto-L-gulonic acid, which was then subjected to distillation under reduced pressure by means of a Soxhlet extractor to eliminate about 2.5 ml (weight: 2.4 g) as distillate (aqueous layer). It was revealed that the aqueous layer was opposed of water (1.4 g), acetone (0.8 g) and HCl (0.1 g). The solution was stirred for 3 hours at the same temperature, which was cooled to 30° C., followed by collecting the resulting precipitates by filtration. The precipitates were washed with a small volume of benzene, then dried under reduced pressure to obtain a grayish crude L-asoorbic acid (13.4 g) (purity: 94.2%, yield: 93.4%) This crystalline crude product contained 2-keto-L-gulonic acid (0.16 g)(remaining ratio: 1%). This crude crystalline product was dissolved in water, and the absorbance ($E_{430nm}^{1\%}$) of the aqueous solution was 0.145. The mother liquor was subjected to extraction twice with 50 ml each portion of water. The aqueous layer was subjected to a high performance liquid chromatography to quantitatively determine the L-ascorbic acid to reveal that the yield was 0.23 g (1.7%), while the 2-keto-L-gulonic acid was detected in an amount of 0.36 g (remaining ratio 2.4%).

EXAMPLE 9

To a mixture solvent of toluene (120 ml) and acetone (10 ml) in which was dissolved hydrogen chloride (3 g) was added 2-keto-L-gulonic acid (purity: 91.2%, water content: 8.4%)(30 g) to which was added trimethylcetylammonium chloride (300 mg), then the whole mixture was heated to 65° C. To the reaction mixture was added 35% HCl (3 ml)(d= 117, 1.23 g as HCl). The water content in the reaction mixture was calculated to be 4.8 ml (1.89 times as much in molar ratio relative to 2-keto-L-gulonic acid). The reaction mixture was stirred for about one hour, then about 1.5 ml (weight: 1.3 g) of water layer was distilled off under reduced pressure. The water layer was composed of water (0.3 g), acetone (0.9 g) and HCl (0.1 g). The reaction mixture was stirred for 3 hours at the same temperature, which was then cooled to 30° C. or below, followed by extraction twice with 300 ml each portion of water. The aqueous layers were combined and subjected to a high performance liquid chromatography to find that L-ascorbic acid was produced in an amount of 23.5 g (yield: 94.9%), while the 2-keto-L-gulonic acid remained unreacted in an amount of 0.4 g (remaining ratio: 1.5%). The absorbance ($E_{430nm}^{1\%}$) of the extract solution was 0.19.

EXAMPLE 10

To a mixture solution of toluene (580 ml) and acetone (30 ml) dissolving therein hydrogen chloride (11.1 g) was added 2-keto-L-gulonic acid (content: 89.9%, water content: 8.4%), (100 g), to which were further added 35% hydrochloric acid (11.8 g)(d=1.17, 4.1 g as HCl) and trimethylcetyl ammonium chloride (0.12 g). The water content in the reaction micture was calculated to be 16.1 ml (1.93 times as much in molar ratio relative to 2-keto-L-gulonic acid). The reaction mixture was stirred for six hours at 60° C., which was then cooled to 20° C. and poured into water (1 l). The whole mixture was stirred, which was then left standing, followed by separating the aqueous layer. To the organic layer was added water (400 ml) for re-extraction. The aqueous layers were combined and subjected to a high performance liquid chromatography for quantitative determination to find that L-ascorbic acid was produced in an amount of 76.6 g (yield: 93.9%), while the 2-keto-L-gulonic acid was remianed unreacted in an amount of 1.4%. The absorbance ($E_{430nm}^{1\%}$) of this aqueous extract was 0.168.

EXAMPLE 11

To a mixture solvent of toluene (580 ml) and acetone (110 ml) dissolving therein hydrogen chloride (11.1 g) was added 2-keto-L-gulonic acid (content: 89.9%, water content: 8.4%) (100 g), to which were added 35% hydrochloric acid (11.8 g) (d=1.17, 4.1 g as HCl) and trimethylcetylammonium chloride (0.12 g). The water content in the reaciton mixture was calculated to be 16.1 ml (1.93 times as much in molar ratio relative to 2-keto-L-gulonic acid). The reaction mixture was heated to 60° C. and stirred for six hours, which was cooled to 20° C. and poured into water (1 l). The reaction mixture was stirred and left standing, followed by separation of the aqueous layer. To the organic layer was added water (400 ml) for re-extraction. The aqueous layers were combined. The L-ascorbic acid produced was quantitatively determined by means of a high performance liquid chromatography to find that the compound was produced in an amount of 74.6 g (yield: 91.5%), while 2-keto-L-gulonic acid remained unreacted in an amount of 2.5%. The absorbance ($E_{430nm}^{1\%}$) of this aqueous extract was 0.135.

COMPARATIVE EXAMPLE 1

In benzene (180 ml) was suspended 2-keto-L-gulonic acid (content: 91.2%, water content: 8.4%) (32 g), to which was added trimethylcetylammonium chloride (140 mg) and then was added 35% hydrochloric acid (10 ml)(d=1.17, 4.09 g as HCl). The water content in the reaction mixture was calculated to be 10.3 ml (3.8 times as much in molar ratio relative to 2-keto-L-gulonic acid).

The reaction mixture was heated to 60° C., which was then stirred for about one hourlthen crystals of 2-keto-L-gulonic acid became oily, followed by distilling off water layer (ca. 8 ml) by means of a Soxhlet extractor under reduced pressure. The residue was stirred for further 5 hours at the same temperature, which was then cooled to 30° C. The reaction mixture was poured into water (300 ml) which was left standing, followed by separating the aqueous layer. To the organic layer was added water (200 ml) for re-extraction.

The aqueous layers were combined and subjected to a high performance liquid chromatography for quantitative determination of L-ascorbic acid to reveal that the compound (22.1 g) (yield: 83.5%) was present, while the 2-keto-L-gulonic acid remained unreacted (1.3%). The absorbance ($E_{430nm}^{1\%}$) of this reaction mixture was 0.45.

COMPARATIVE EXAMPLE 2

In toluene (80 ml) was suspended 2-keto-L-gulonic acid (content: 92.1%, water content: 8.3%)(20 g), to which was added hexadecyl trimethylammonium chloride (200 mg), and the mixture was heated to 65° C. To the mixture was further added 35% hydrochloric acid (1.2 ml), followed by introducing hydrogen chloride for 150 minutes at a rate of 80 ml/min. The solvent was then distilled off under reduced pressure at temperatures not exceeding 30° C. To the residue was added toluene (100 ml), and the mixture was sufficiently stirred, followed by distilling off the solvent under reduced pressure at temperatures not exceeding 30° C. To the residue was again added toluene (100 ml), and the mixture was sufficiently stirred, followed by cooling to temperatures not exceeding 20° C. Resulting precipitates were collected by filtration, washed with a small volume of toluene, and then dried under reduced pressure.

The product was dissolved in water (300 ml), which was subjected to a high performance liquid chromatography for quantitative determination of the L-ascorbic acid produced to reveal that the compound was present in an amount of 14.1 g (yield: 84.4%), while no 2-keto-L-gulonic acid was detected The absorption ($E_{430nm}^{1\%}$) of ths aqueous solution was 0.47.

The mother liquor was concentrated to dryness under reduced pressure, and the residue was dissolved in water (300 ml). Qauntitative determination of ascorbic acid by means of a high performance liquid chromatogrpahy revealed the existence of the compound (0.18 g)(yield: 1.1%).

COMPARATIVE EXAMPLE 3

To toluene (552 ml) was added 2-keto-L-gulotic acid (content: 91.2%, water content: 8.4%)(92.4 g). To the mixture was added trimethylcetyl ammonium chloride (100 mg), to which was further added 35% concentrated hydrochloric acid (9.4 ml)(d=1.17, 3.85 g as HCl, 7.1 g as water). The volume of water contained in the reaction mixture was calculated to be 14.9 g (1.90 times as much in molar ratio relative to 2-keto-L-gulonic acid). Into the reaction mixture was blown, while heating at 60° C., hydrogen chloride (10.4 g) taking six hours, followed by cooling to 20° C. (the total acid amount relative to 2-keto-L-gulonic acid was 0.9 times as much in molar ratio) The amount of L-ascorbic acid produced by processing the reaction mixture in a manner similar to Example 1 was found to be 30.6 g (yield: 40%) by a high performance liquid chromatography for quantitative determination The amount of 2-keto-L-gulonic acid remaining unreacted was 46.3 g (remaining ratio 55%). The absorbance ($E_{430nm}^{1\%}$) of this extract solution was 0.12.

COMPARATIVE EXAMPLE 4

To a mixture solvent of toluene (550 ml) and acetone (40 ml) was added 2-keto-L-gulonic acid (content: 91.2%, water content: 8.4%)(92.4 g), to which was then added trimethylcetyl ammonium chloride (100 mg), followed by further addition of 35% conc. hydrochloric acid (11 ml)(d=1.17, 4.55 g as HCl, 8.45 g as water). The reaction mixture was heated to 60° C. and stirred for one hour, followed by addition of an acetone solution (200 g)(containing 9.55 g of hydrogen chloride). The whole mixture was stirred for 5 hours at the same temperature, then cooled to 20° C. (the total acid amount relative to 2-keto-L-gulonic acid was 0.9 times as much in molar ratio)

The reaction mixture was processed in a manner similar to that of Example 1 to produce L-ascorbic acid, which was subjected to quantitative determination by means of a high performance liquid chromatography to find that the amount of the compound was 64.9 g (yield: 84.9%). The amount of 2-keto-L-gulonic acid remaining unreacted was 8.4 g (remaining ratio: 10.0%). The absorbance ($E_{430nm}^{1\%}$) of this extract solution was 1.5.

We claim:

1. A method of preparing L-ascorbic acid, which comprises allowing an acid to act on 2-keto-L-gulonic acid in a mixed solvent consisting essentially of an inert organic solvent and an aliphatic ketone in the presence of water and a surfactant wherein the volume of the aliphatic ketone in the mixed solvent is in a range of 0.02 to 0.3 relative to the volume of the inert organic solvent, and wherein the amount of water is 1.5 to 3.5 times as much in molar ratio relative to 2-keto-L-gulonic acids and the amount of the acid is 0.5 to 2 times as much in molar ratio relative to 2-keto-L-gulonic acid.

2. The method claimed in claim 1, wherein the inert organic solvent is an aromatic hydrocarbon.

3. A method claimed in claim 1, wherein the aliphatic ketone is a ketone having an alkyl whose carbon number is 1 to 6 or a cyclic ketone having a cycloalkyl whose carbon number is 5 to 6.

4. A method claimed in claim 1, wherein the acid is hydrochloric acid.

5. The method claimed in claim 1, wherein the surfactant is a quarternary ammonium salt.

* * * * *